(12) United States Patent
Webb et al.

(10) Patent No.: US 8,664,623 B2
(45) Date of Patent: Mar. 4, 2014

(54) FLUORESCENCE MEASUREMENT

(75) Inventors: Stephen Edwin Dominic Webb, Warrington (GB); Marisa Martin-Fernandez, Warrington (GB)

(73) Assignee: The Science and Technology Facilities Council, Daresbury (GB)

( * ) Notice: Subject to any disclaimer, the term of this patent is extended or adjusted under 35 U.S.C. 154(b) by 1082 days.

(21) Appl. No.: 12/595,094

(22) PCT Filed: Apr. 9, 2008

(86) PCT No.: PCT/GB2008/001221
§ 371 (c)(1),
(2), (4) Date: Jan. 18, 2010

(87) PCT Pub. No.: WO2008/129233
PCT Pub. Date: Oct. 30, 2008

(65) Prior Publication Data
US 2010/0140504 A1 Jun. 10, 2010

(30) Foreign Application Priority Data

Apr. 18, 2007 (GB) .................................. 0707433.9

(51) Int. Cl.
*G01N 21/64* (2006.01)
*G01J 1/58* (2006.01)
(52) U.S. Cl.
USPC ..................................... 250/458.1; 250/459.1
(58) Field of Classification Search
USPC ........................................... 250/458.1, 459.1
See application file for complete search history.

(56) References Cited

U.S. PATENT DOCUMENTS

| | | | | |
|---|---|---|---|---|
| 4,643,566 | A | * | 2/1987 | Ohe et al. .......................... 356/72 |
| 4,916,319 | A | * | 4/1990 | Telfair et al. ................ 250/461.1 |
| 5,026,996 | A | * | 6/1991 | Fricke ......................... 250/461.1 |
| 5,880,465 | A | * | 3/1999 | Boettner et al. ............... 250/234 |
| 6,566,143 | B2 | * | 5/2003 | Hoyt .............................. 436/172 |
| 2001/0049473 | A1 | | 12/2001 | Hayashi |
| 2004/0125372 | A1 | * | 7/2004 | Walla et al. .................... 356/318 |
| 2007/0016078 | A1 | * | 1/2007 | Hoyt et al. ..................... 600/476 |

FOREIGN PATENT DOCUMENTS

| | | |
|---|---|---|
| EP | 1 256 310 A2 | 11/2002 |
| JP | H02-226057 A | 9/1990 |

OTHER PUBLICATIONS

Carl Zeiss Inc. Multi-Color TIRF. [retrieved Jul. 24, 2006]. Retrieved from the Internet: <URL: http://www.zeiss.com>.
Confocal microscopy—Wikipedia, the free encyclopedia. [retrieved May 3, 2007]. Retrieved from the Internet: <URL: http://en.wikipedia.org/wiki/Confocal_microscopy>.

(Continued)

*Primary Examiner* — David Porta
*Assistant Examiner* — Mindy Vu
(74) *Attorney, Agent, or Firm* — Woodard, Emhardt, Moriarty, McNett & Henry LLP

(57) ABSTRACT

Methods and apparatus for measuring fluorescence, are described. The method includes measuring at least one profile of at least a portion of a surface of a sample, the surface extending substantially transverse an axis, and illuminating the portion of the sample surface with radiation for stimulating fluorescence. The intensity of the radiation varies with position along the axis. Values indicative of the spatial intensity distribution of fluorescence emitted from said portion of the sample surface are measured. The measured values of fluorescence are modified to take account of the spatial variation in intensity of radiation incident upon the surface by utilizing the measured profile.

16 Claims, 4 Drawing Sheets

(56) References Cited

OTHER PUBLICATIONS

Document: Laser Wavelengths. [retrieved Jul. 24, 2006]. Retrieved from the Internet: <URL: http://www.zeiss.com/de/micro/home_e.nsf/allBySubject>.

Document: Principle. "The principle of TIRF microscopy". [retrieved Jul. 24, 2006]. Retrieved from the Internet: <URL: http://www.zeiss.com/de/micro/home_e.nsf/allBySubject>.

Evanescent wave—Wikipedia, the free encyclopedia. [retrieved Aug. 3, 2007]. Retrieved from the Internet: <URL: http://en.wikipedia.org/wiki/Evanescent>.

Fluoescence resonance energy transfer—Wikipedia, the free encyclopedia. [retrieved Aug. 3, 2007]. Retrieved from the Internet: <URL: http://en.wikipedia.org/wiki/Fluorescence_resonance_energy_transfer>.

Forkey, Joseph N. et al., "Measurement of Single Macromolecule Orientation by Total Internal Reflection Fluorescence Polarization Microscopy", Biophyiscal Journal, vol. 89, Aug. 2005, 1261-1271.

Forkey, Joseph N. et al., "Protein structural dynamics by single-molecule fluorescence polarization", Progress in Biophysics & Molecular Biology, 74 (2000) 1-35.

Groves, Jay T., "Bending Mechanics and Molecular Organization in Biological Membranes," Annu. Rev. Phys. Chem., vol. 58, pp. 697-717, Jan. 2, 2007.

Homodyne detection—Wikipedia, the free encyclopedia. [retrieved Jun. 3, 2007]. Retrieved from the Internet: <URL: http://en.wikipedia.org/wiki/Homodyne_detection>.

International Application PCT/GB2008/001221 International Search Report and Written Opinion mailed Jul. 1, 2008.

JP H02-226057 A English Language Abstract.

Lee, Chauh-Wang et al., "Noninterferometric wide-field optical profilometry with nanometer depth resolution", Optics Letters, vol. 27, No. 20, pp. 1773-1775, Oct. 15, 2002.

Lee, Chau-Hwang et al., "Using differential confocal microscopy to detect the phase transition of lipd vesicle membranes", Society of Photo-Optical Instrumentation Engineers Opt. Eng. 40(10), Oct. 2001, 2077-2063.

Light sources. [retrieved Jul. 24, 2006]. Retrieved from the Internet: <URL: http://www.andor.com/products/accessories/?app=220>. (follow "Light Sources/View Details" hyperlink).

Microscopy—Wikipedia, the free encyclopedia. [retrieved May 3, 2007]. Retrieved from the Internet: <URL: http://en.wikipedia.org/wiki/Microscopy>.

RGB (Red/Green/Blue) Combiner and Delivery Systems. [Jun. 10, 2005] Retrieved from the Internet: <URL: http://www.ozoptics.com/ALLNEW_PDF/DTS0105.pdf.>.

Sako, Yasushi et al., "Single-molecule imaging of EGFR signalling on the surface of living cells", Nature Cell Biology, vol. 2, Mar. 2000.

Sarkar, Atom et al., "Simultaneous atomic force microscope and fluorescence measurements of protein unfolding using a cliabrated evanescent wave", PNAS, Aug. 31, 2004, vol. 101, No. 35, 12882-12886.

Siegel, J. et al., "Whole-field five-dimensional fluorescence microscopy combining lifetime and spectral resolution with optical sectioning," Optics Letters, vol. 26, No. 17, pp. 1338-1340, Sep. 1, 2001.

TIRF. "Discover more with Laser TIRF" [retrieved Jul. 24, 2006]. Retrieved from the Internet: <URL: http://www.zeiss.com/de/micro/home_e.nsf/allBySubject>.

Total internal reflection fluorescence microscope—Wikipedia, the free encyclopedia. [retrieved Aug. 3, 2007]. Retrieved from the Internet: <URL: http://en.wikipedia.org/wiki/Total_internal_reflection_fluorescence_microscope>.

United Kingdom Patent Application GB0707433 Search Report mailed Aug. 20, 2007.

Wang, Chun-Chieh et al., "Dynamics of cell membranes and the underlying cytoskeletoncs observed by noninterferometric widefield optical profilometry and fluorescence microscopy," Optics Letters Opt. Soc. America USA, vol. 31, No. 19, pp. 2873-2875, Oct. 1, 2006.

Wang, Chun-Chieh et al., "Membrane ripples of a living cell measured by non-interferometric widefield optical profilometry", Optics Express, vol. 13, No. 26, Dec. 26, 2005.

We make light work. [retrieved Jul. 24, 2006]. Retrieved from the Internet: <URL: http://www.displaytech.com/photonics_rotators.html>.

Webb, S.D. et al., "Multidimensional single-molecule imaging in live cells using total-internal-reflection fluorescence microscopy", Optics Letters, vol. 31 Issue 14, pp. 2157-2159 (2006).

Webb, S.E.D. et al., Multidimensional single-molecule imaging in live cells using total-internal-reflection fluorescence microscopy. Optics InfoBase—Published by the Optical Society of America [online], 2006. [retrieved Jul. 24, 2006]. Retrieved from the Internet: <URL: http:www.opticsinfobase.org/abstract.cfm?URL=ol-31-14-2157>.

Wong, Amy P. et al., "Topographical Imaging of an Intermembrane Junction by Combined Fluoescence Intererence and Energy Transfer Microscopies," J. Am. Chem. Soc., vol. 123, No. 49, pp. 12414-12415, 2001.

* cited by examiner

FLUORESCENCE MEASUREMENT

This application is the National Stage of International Application No. PCT/GB2008/001221, filed Apr. 9, 2008, which claims the benefit of United Kingdom Application No. GB 0707433.9, filed Apr. 18, 2007.

The present invention relates to methods and apparatus suitable for measuring fluorescence. The invention is particularly suitable for, but not limited to, application to TIRF (Total Internal Reflection Fluorescence) microscopy, including TIRF microscopy of cell membranes.

Fluorescence is an emission of electromagnetic radiation from a material, following excitation of that material by electromagnetic radiation, or the impact of electrons. Normally, the excitation radiation is of higher energy (higher frequency or shorter wavelength) than the emitted radiation.

Typically, the excitation radiation and the emitted radiation will be within the visible range. Fluorescence measurements can be used to provide a greater understanding of the structure and/or function of materials.

For example, fluorescence microscopy is a form of microscopy in which the specimen is irradiated at wavelengths which will excite fluorophores (or fluorochromes) within the specimen. The fluorophores may be naturally occurring within the specimen, or may be artificially introduced. For example, biological molecules can have a fluorescent chemical group (commonly referred to as a "tag") attached by a chemical reaction. The study of the resulting fluorescent image can provide useful information regarding the specimen.

TIRF microscopy is a specialised form of fluorescence microscopy that can be utilised to examine processes in cell membranes, and obtain knowledge about the molecular mechanisms at the boundary to the cell interior.

TIRF microscopy uses an evanescent wave to selectively illuminate and excite fluorophores in a restricted region of the specimen. The specimen will typically be mounted on, or adjacent, an optical element such as a prism or a glass cover slip. Excitation light is provided into the optical element, such that the light undergoes total internal reflection from the surface of the optical element adjacent the specimen. An evanescent electromagnetic field is thus generated that decays exponentially from the surface of the optical element, and typically propagates to a depth of the order of hundreds of nanometers into the adjacent specimen. The evanescent field can thus be used to excite fluorophores in a restricted region of the specimen immediately adjacent to the optical element. This selectivity of the excitation region is advantageous compared with conventional fluorescence microscopes. In conventional techniques the fluorescence from fluorophores bound to surfaces of specimens can often be overwhelmed by the background fluorescence.

TIRF microscopy has been used to measure single fluorescent molecules in cell membranes, and is a technique that allows the observation of such single molecules in the normal physiological environment of living cells. For example, the article by S. E. D. Webb et al., "Multidimensional single-molecule imaging in live cells using total-internal-reflection fluorescence microscopy", OPTICS LETTERS, Vol. 31, No. 14, pp 2157-2159, describes the development of a wide-field TIRF microscope capable of imaging single molecules in live cells, resolved in both wavelength and polarisation.

It is an aim of embodiments of the present invention to substantially address one or more problems of the prior art, whether described herein or otherwise. It is an aim of particular embodiments of the present invention to improve TIRF microscopy.

In a first aspect, the present invention provides a method of measuring fluorescence from a sample, comprising the steps of: measuring at least one profile of at least a portion of a surface of a sample, the surface extending substantially transverse an axis; illuminating said portion of the surface of the sample with radiation for stimulating fluorescence, the intensity of the radiation varying with position along the axis; measuring values indicative of the spatial intensity distribution of fluorescence emitted from said portion of the sample surface; and modifying the measured values of fluorescence to take account of the spatial variations in intensity of radiation incident upon the surface by utilising said measured profile.

The present inventors have realised that fluorescence measurement techniques (such as TIRF microscopy), in which the intensity of the excitation radiation varies with position, can be improved by taking into account the intensity of radiation actually incident upon each fluorophore. Typically, in such measurements, the surface of the specimen is uneven. As the intensity of the excitation radiation varies with position, different portions of the surface (e.g. portions at different heights) will experience different intensities of excitation radiation. Such fluorescence measurements can thus be improved by taking into account the actual intensity incident upon the different specimen surface positions (i.e. and hence incident upon the different fluorophores within the surface). Such an approach permits the quantitative measurement of the fluorescence from different positions on the surface.

Said modifying step may comprise calculating the spatial variation in intensity of radiation incident on said surface from said measured profile and from information indicative of the variation of the radiation beam intensity with position along the axis.

Said sample may be positioned adjacent an optical element, the illuminating step comprising: providing a radiation beam arranged to undergo total internal reflection within said optical element so as to produce an evanescent field of radiation for exciting fluorophores on the sample surface.

Said radiation beam may be split into two sub-beams, each arranged to undergo total internal reflection in a respective reflection plane.

Said step of illuminating said portion of the sample surface may comprise providing said radiation in a first polarisation state, and said step of measuring values may comprise measuring values indicative of the spatial intensity distribution of fluorescence emitted in a first polarisation state from said portion of the sample surface, and measuring values indicative of the spatial intensity distribution of fluorescence emitted in a second, different polarisation state from said portion of the sample surface.

The step of illuminating said portion of the sample surface may further comprise subsequently providing said radiation in a second, different polarisation state for stimulating fluorescence.

Said step of measuring values may comprise: measuring values indicative of the spatial intensity distribution of fluorescence emitted in a first wavelength range from said portion of the sample surface, and measuring values indicative of the spatial intensity distribution of fluorescence emitted in a second, different wavelength range from said portion of the sample surface.

The steps of measuring said profile and measuring said values indicative of the spatial intensity distribution of fluorescence may be both repeated over a period of time, for monitoring changes in the conformation of said sample.

The steps of measuring said profile and measuring values indicative of the spatial intensity distribution of fluorescence may be performed simultaneously.

The step of measuring said profile may comprise: illuminating said portion of the sample with a radiation beam, and measuring the spatial variation in intensity of the reflected radiation beam.

Said step of measuring said profile may comprise measuring the topography of said at least a portion of the surface of the sample.

Said topography may be measured by non-interferometric widefield optical profilometry.

Said topography may be measured by wide-field optically sectioning microscopy.

Said sample may be a biological cell, the surface of which is defined by a cell membrane.

In a second aspect, the present invention provides an apparatus for measuring fluorescence from a sample, the apparatus comprising: a sample holder for holding a sample such that at least a portion of a surface of the sample extends substantially transverse a predetermined axis; a profilometer for measuring at least one profile of said portion of the surface of the sample; a radiation source for illuminating said portion of the surface of the sample with radiation for stimulating fluorescence, the intensity of the radiation varying with position along the axis; a detector arranged to measure values indicative of the spatial intensity distribution of fluorescence emitted from said portion of the sample surface; and a processor arranged to modify the measured values of fluorescence to take account of the spatial variations in intensity of radiation incident upon the surface by utilising the measured profile.

In a third aspect, the present invention provides a device for controlling an optical apparatus to carry out a fluorescence measurement, the device comprising: a program memory containing processor readable instructions; and a processor configured to read and execute instructions stored in said program memory, wherein said processor readable instructions comprise instructions configured to control said apparatus to carry out a method as described above.

In a fourth aspect, the present invention provides a carrier medium carrying computer readable code configured to cause a computer to carry out a method as described above.

Preferred embodiments of the present invention will now be described, by way of example only, with reference to the accompanying drawings, in which.

In some fluorescence measurement techniques, such as TIRF (Total Internal Reflection Fluorescence) the intensity of the radiation used to excite the sample varies with position. As the intensity of the fluorescence is dependent upon the intensity of the excitation radiation (i.e. the radiation used to stimulate the fluorescence), to allow an accurate assessment of the fluorescence emissions, the present inventors have realised that it is desirable to measure the profile of the sample surface, so as to allow the intensity of excitation radiation incident upon the surface at different positions to be taken into account when assessing the resulting measured values of fluorescence.

Figure 2:
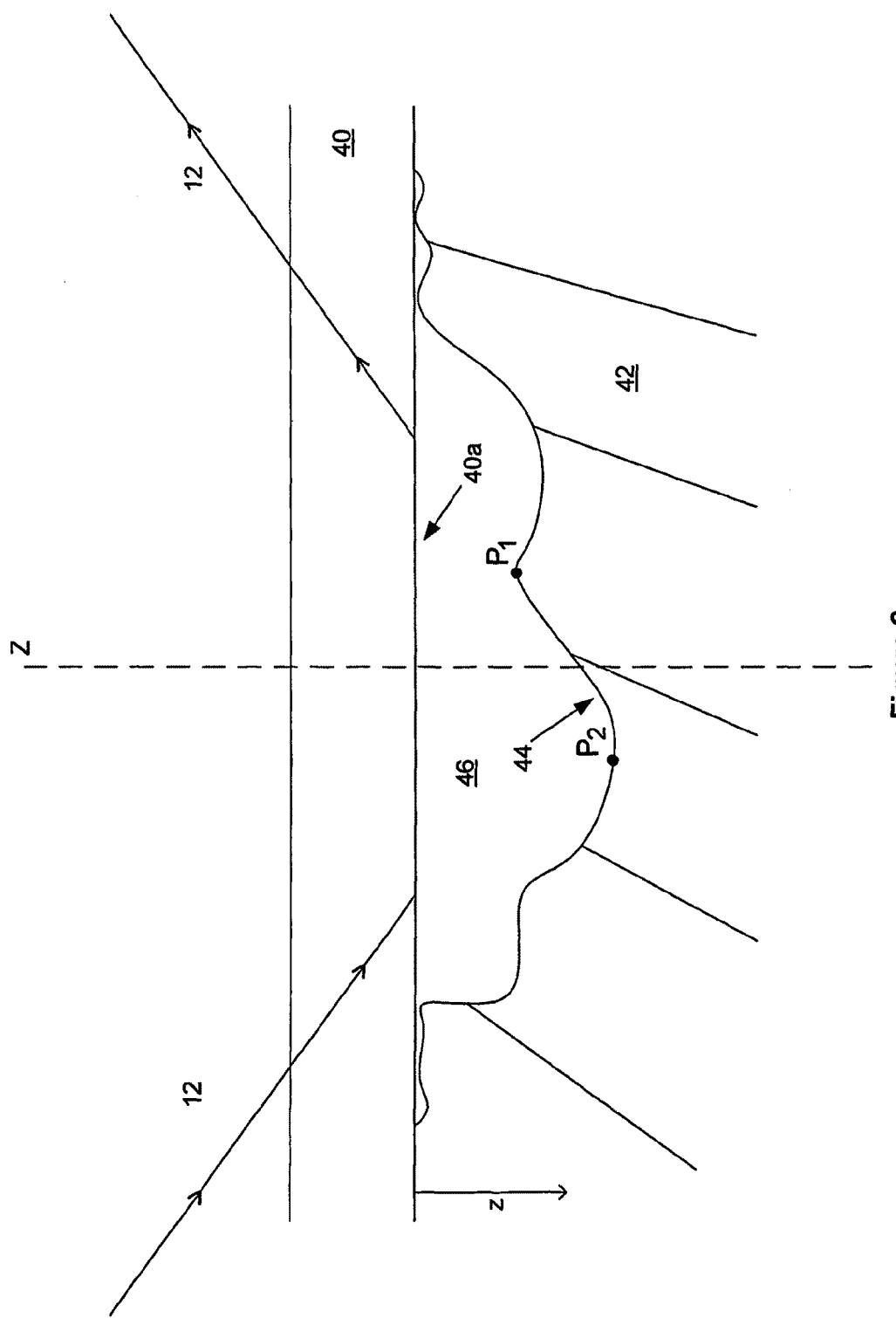
FIG. 2 is a magnified view of the specimen positioned in the sampling position shown in FIG. 1.

For example, FIG. 2 is a magnified view of a portion of a sample 42 mounted on an optical element (here, a cover slip 40). The sample 42 is located in a sample medium 46, which can be an aqueous solution. The sample 42 has a surface 44 that extends generally transverse an optical axis Z. The surface 44 of the sample is non-linear e.g. it is ruffled. Hence the distance between molecules in the surface of the sample will vary in their position along the axis Z.

In this example, the cover slip 40 extends substantially perpendicular to the axis Z. The surface 44 is shown as comprising two fluorophores, $P_1$, $P_2$. The fluorophores are at different positions along the Z axis.

A beam of radiation 12 of suitable wavelength to stimulate the fluorophores to fluoresce is incident on the cover slip 40. The angle of incidence of the radiation beam 12 is selected such that the radiation beam 12 undergoes total internal reflection at the cover slip surface 40a. This total internal reflection results in an evanescent electromagnetic wave or field extending from the surface 40a of the cover slip adjacent to the sample 42. The evanescent electromagnetic field decays exponentially from the surface 40a, and will thus typically only propagate a distance of around 100-300 nanometers in the direction of the sample (as indicated by the arrow z). Thus, the intensity of the excitation radiation (the evanescent field) changes with position along the axis Z, and in particular decreases in the direction illustrated by the arrow z. Thus, the fluorophore $P_1$, which is closest to the surface 40a from which the evanescent field propagates, will experience a higher intensity of the evanescent field than fluorophore $P_2$.

Different fluorophores can have different quantum yields. Quantum yield is the ratio of the number of fluorescent photons to the total number of absorbed excitation photons. The quantum yield of a fluorophore may also change if energy can be transferred to other neighbouring fluorophores. Thus, to evaluate the quantum yield of fluorophores $P_1$ and $P_2$ (and indeed, the number of fluorophores that may be located at a given position/within a predetermined area of the surface), it is necessary to determine the incident intensity of excitation radiation at the position of each fluorophore $P_1$, $P_2$. Equally, such information can also be used to determine whether a plurality of fluorophores is located at different positions (or at least within predetermined areas) on the surface of the sample. Further, by monitoring the fluorescence from the surface in conjunction with the profile of the surface over time, changes in the conformation of molecules on the surface may be correlated with changes to the surface profile.

Such a technique would be particularly valuable for analysing the effect of drugs on processes (such as cell signalling) under physiological conditions i.e. using live cells and low receptor densities, and allowing the examination of relatively rare or unsynchronised events. For example, during the cell signalling process, ligand protein molecules (e.g. epidermal growth factor, EGF) dock on to the extracellular domain of transmembrane proteins (e.g. EGF receptor, EGFR, also known as HER1 or ErbB1) causing intracellular interactions and hence transmission of the signal to the nucleus. Such a process may be accompanied by conformational changes of the receptor molecules and changes in the oligomerisation state of the molecules.

Utilising the process described above, in which the profile of the sample (e.g. cell) is measured, allows any correlation between receptor clustering and membrane ruffles to be identified. Conformational changes in the cells can be identified in a TIRF microscope by measuring fluorescence resonance energy transfer (FRET). Examination of the polarisation of the fluorescence can be used to see distance and angle changes within and between proteins. Further, if the polarisation of the fluorescence radiation is monitored, then any change in the polarisation of the fluorescence due to receptor conformational changes could be distinguished from changes in the orientation of the receptors following membrane reshaping.

Particular implementations of the present invention will now be described, with reference to the accompanying Figures.

Figure 1:
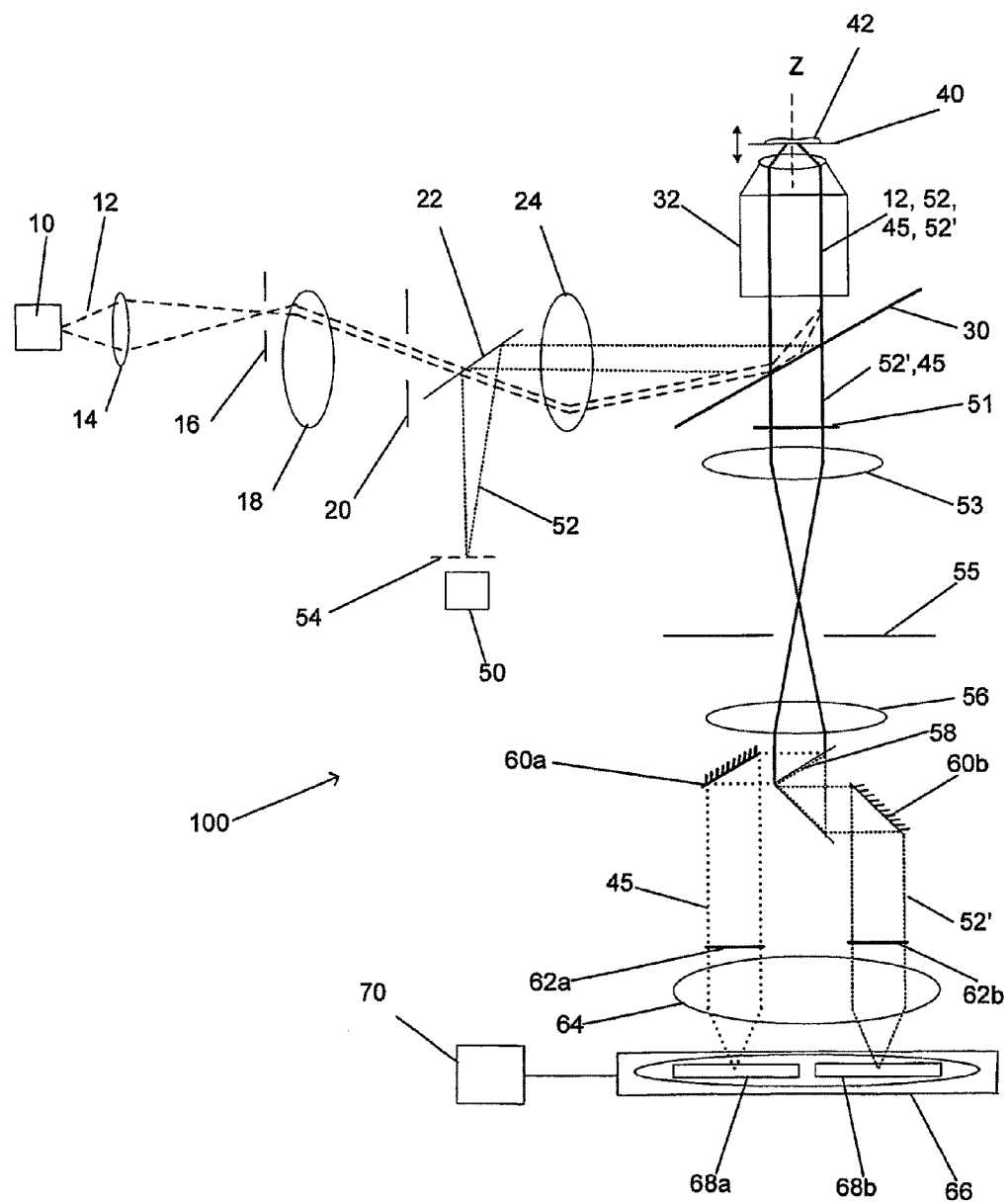
FIG. 1 is a schematic diagram illustrating an apparatus for measuring the fluorescence of a specimen in accordance with an embodiment of the present invention.

FIG. 1 shows an apparatus 100 for measuring fluorescence, in accordance with an embodiment of the present invention. The apparatus 100 is arranged to simultaneously measure the profile of a sample surface, and measure the spatial distribution in fluorescence from that surface. Although both of these operations could be carried out by separate apparatus in a sequential manner, providing a single apparatus to perform both operations allows the dual use of components, and the operations to be performed simultaneously. Simultaneous measurement is desirable if the sample can undergo conformation changes. Such simultaneous operation is particularly desirable when the measurements are repeated over a period of time (e.g. at regular intervals) that allows the study of the changes in conformation of the specimen or sample. For example, measurements could be repeated every second or less, or every 100 milliseconds, or even every 30 milliseconds or less on biological samples.

The components of the apparatus 100 shown in FIG. 1 will now be described. Firstly, the components and optical elements for providing the fluorescence excitation radiation will be described.

The apparatus 100 includes a radiation source 10 for providing a beam 12 of electromagnetic radiation of predetermined wavelength (or of a predetermined range of wavelengths) for excitation of one or more types of fluorophore. The radiation is provided such that a portion of the surface of the sample is illuminated with radiation for stimulating the fluorescence. In this particular example, TIRF microscopy is utilised, and hence the radiation beam 12 is directed into an optical element (here, a cover slip 40) at the surface of which the radiation beam undergoes total internal reflection. The resulting evanescent field is used to excite the fluorophores within the sample 42.

Varies optical arrangements could be utilised to provide the radiation beam 12 to the optical element 40. In this particular embodiment, the optical path between the radiation source 10 and the optical element 40, through which the radiation beam 12 passes, includes beam-shaping lenses 14, 18 & 24, and an objective lens 32. The beam also passes through spatial filter 16 to ensure a Gaussian beam profile and aperture 20 to vary the diameter of the beam at the sample 42. The beam passes through a dichroic beam splitter 22. The dichroic beam splitter 22 is utilised to combine the optical path of radiation 12 used to excite the fluorophores, with the path of the radiation beam 52 used to measure the profile of the surface 44 of the sample 42.

The apparatus 100 additionally incorporates apparatus used to measure the profile of the surface 44 of sample 42.

To allow simultaneous measurement of the profile of the surface 44, and fluorescence from the surface (or at least from fluorophores within the surface) the profile is preferably measured using an optical technique. Such optical techniques involve illuminating the relevant surface of the sample with the radiation beam, and measuring the spatial variation in intensity from the reflected radiation beam (e.g. from the image formed by the reflective beam incident on a detector such as a CCD, Charged-Coupled Device).

A number of suitable optical profiling techniques and apparatus are known, such as white-light interferometric profilers, or noninterferometric optical profilers such as differential confocal microscopy (DCM), or the technique of wide-field optically sectioning microscopy. Any of these techniques can be utilised. However, in the particular apparatus illustrated in FIG. 1, the apparatus is arranged to perform noninterferometric wide-field optical profilometry (NIWOP). Such a technique can be used to provide nanometer depth resolution of the sample. NIWOP techniques and apparatus are, for instance, described within the articles: (1) Wang, C. C., Lin, J. Y. & Lee, C. H. "Membrane ripples of a living cell measured by non-interferometric widefield optical profilometry", Optics Express 13, 10665-10672 (2005), and (2) Lee, C. H., Mong, H. Y. & Lin, W. C. "Noninterferometric wide-field optical profilometry with nanometer depth resolution", Optics Letters 27, 1773-1775 (2002), the contents of both of which are incorporated herein by reference.

Radiation source 50 provides the radiation beam 52 for the NIWOP profilometry measurement. The technique utilises the imaging of a grid pattern, in three different phase positions, on to the sample surface 44. The grid pattern is provided by a grating 54 located in the optical path of beam 52. The grating includes a translation stage, to allow movement of the grating both along the optical axis of the beam 52, and transverse to the optical axis (i.e. to alter the phase). The transverse movement of the grating can be utilised to provide the three grid patterns at different phases on the sample surface 44, the images of which are used to measure the sample surface profile in three dimensions (i.e. to measure the topography of the surface 44).

Radiation beam 52 is introduced into a common optical path as the radiation beam 12 (so beams 12 & 52 pass through common optical elements) by dichroic beam splitter 22. Dichroic beam splitter 22 is arranged to transmit the wavelength(s) of beam 12, and to reflect the wavelength(s) of beam 52. Both beams 12, 52 are directed into the objective lens 32 by a further dichroic beam splitter 30. Dichroic beam splitter 30 is arranged to reflect the wavelength(s) of beam 12, and to partially reflect and partially transmit the wavelength(s) of beam 52.

The spatial frequency of the grating 54 is selected so as to allow the use of a single objective lens 32 for both the TIRF microscopy and the profilometry. The wavelength for the radiation beam 52 used for the profilometry is selected such that it does not overlap either with the wavelength(s) of the excitation beam 12, or the anticipated fluorescence emission spectra. The grating 54 has a single spatial frequency, and is positioned adjacent to a conjugate plane to the sample plane. The spatial frequency is selected to maximise the depth resolution over the anticipated range of sample surface profiles, for the objective lens required for TIRF microscopy. For example, for a depth resolution of approximately 2 nm and a depth range of approximately 200 nm, the ideal grating spatial frequency is equal to (numerical aperture of objective lens 32)/(wavelength of radiation beam 52× magnification of objective lens 32).

Profilometry beam 52 will be reflected back from the sample surface as reflected beam 52', and pass back through the objective lens 32, with the reflected image ultimately being detected by detector 66. Evanescent radiation resulting from the total internal reflection of radiation beam 12 will excite fluorophores $P_1$, $P_2$ on the sample surface, leaving the fluorophores to fluoresce i.e. to emit fluorescence 45. The fluorescence 45 will similarly pass through the dichroic filter 30, ultimately to form an image that is detected by the detector 66.

Reflected profilometry radiation beam 52' and the fluorescence emission 45 initially travel along a common optical path to a dichroic beam splitter 58.

In particular, both the reflected beam 52' and the fluorescence travel from the sample surface 42, through objective lens 32, through the dichroic filter 30. The radiation 52', 45 then passes through a filter 51, arranged to pass the fluorescence and reflected wavelengths, and block other wavelengths (such as the wavelength of the excitation beam 12). The reflected beam 52' and the fluorescence 45 then pass through lenses 53 & 56, and an aperture 55, prior to being incident on dichroic filter 58.

Dichroic filter 58 separates the reflected beam 52' from the fluorescence 45 (by being wavelength selective in terms of the wavelengths reflected versus the wavelengths transmitted by the dichroic filter 58). The split radiation signals 52', 45 are then directed along respective optical paths to be imaged on respective sensor areas 68a, 68b of detector 66. In particular, each signal, in this particular arrangement, reflects off a respective mirror 60a, 60b, passes through a filter 62a, 62b (arranged to pass the wavelengths of the respective signal, and block other wavelengths), and is then focussed by a lens (in this example, a lens 64 common to both signals) so as to be imaged on the respective detector areas 68a, 68b.

Figure 3A:
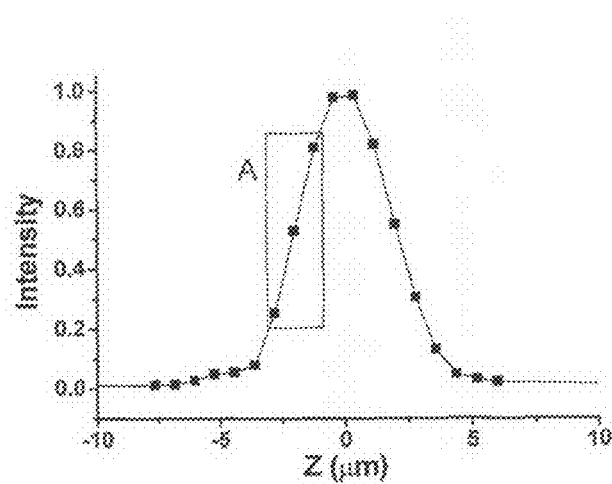
FIG. 3a is a graph illustrating the variation of the intensity of light reflected from a mirror placed in the sample position in FIG. 1, as a function of mirror position along the Z-axis.
Figure 3B:
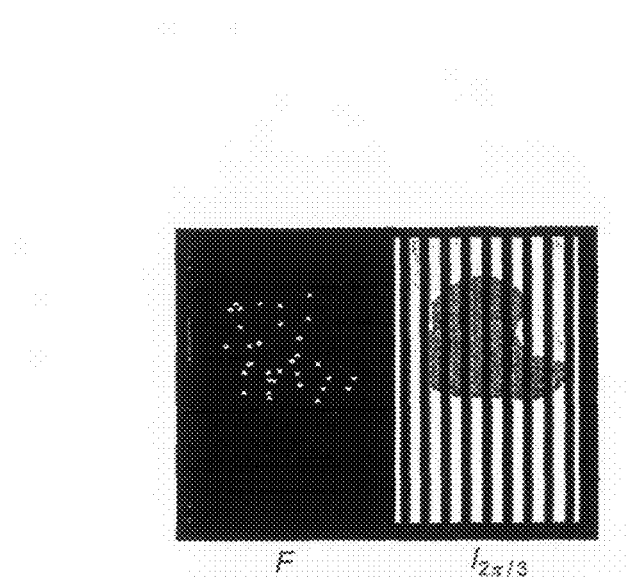
FIG. 3b illustrates the images acquired by the two halves of the CCD detector illustrated in FIG. 1.

The variation in spatial intensity of each image is then measured by the detector 66, and passed to processor 70. FIG. 3B shows an image acquired by detector 66. The left hand side of the image corresponds to the image detected by detector element 68a, and the right hand side to the image detected by detector element 68b. A CCD can be used as detector 66. Both halves of the detector image are identical fields of view. In the particular example shown in FIG. 3B, the sample has a very low concentration of fluorophores on its surface. The left hand side of the image corresponds to the single-molecule fluorescence image. The right hand side image in FIG. 3B is one of the three images used in NIWOP to calculate the profile of the sample surface (the lines on the image are from the grating 54).

Three different images are taken of the reflected radiation, with the grating in different phase positions, to allow the profile of the surface to be calculated.

Processor 70 is arranged to modify the measured values of fluorescence to take account of the spatial variations in intensity of radiation incident upon the surface by utilising the measured profile of the sample surface 40.

In particular, processor 70 is arranged to modify the measured fluorescence values to take account of the variation in the intensity of the evanescent field, by performing the following steps/calculations:

(i) Calculate the sample surface profile.

(ii) From the sample surface profile, calculate the evanescent field strength distribution across the sample surface (i.e. the spatial distribution of the strength excitation radiation incident on the sample surface).

(iii) Modify or "Normalise" the measured fluorescence intensity values by dividing each measured intensity by the evanescent field strength of the sample surface at the spatial position.

The operation of the apparatus 100 will now be briefly described. Firstly, a calibration technique is performed to calibrate the profilometry portion of the apparatus 100. In particular, a plane mirror is placed in the sample plane of the microscope (i.e. approximately in the position normally occupied by the sample 42). Radiation source 10 is disabled, such that only radiation beam 52 is incident on to the sampling position. Three sequential images are required, with the grating 54 at relative spatial phases 0, 2p/3, 4p/3. The sectioned image intensity $I_s$ can be calculated from $$I_s = \frac{3}{\sqrt{2}} [(I_0 - I_{2\pi/3})^2 + (I_0 - I_{4\pi/3})^2 + (I_{2\pi/3} - I_{4\pi/3})^2]^{1/2}$$

where $I_x$ is the image acquired at spatial phase x.

The three images (each image corresponding to a different spatial phase) are then acquired, with the sectioned image $I_s$ calculated, for a series of positions of the plane mirror along the Z-axis. The intensities of the sectioned images $I_s$ can then be plotted as a function of position along the Z-axis, to provide a response curve similar to that shown in FIG. 3A. In FIG. 3A, the position of z=0 has been arbitrarily chosen as the peak image intensity. The rectangle A indicates a portion of the response curve in which the intensity is directly proportional to the position along the mirror along the axis-Z, and has a gradient a.

Once the profilometry apparatus has been calibrated, the sample 42 is placed in the sampling position in front of objective lens 32. The grating 54 is positioned such that it is imaged out-of-focus on to the sample surface 44, but within the linear region A shown in FIG. 3A. As in the initial calibration, three images are obtained, corresponding to the grating being at relative spatial phases 0, 2p/3, 4p/3, and the resulting image intensity $I_{s\,defocused}$ calculated, as per $I_s$ (e.g. from the three different images corresponding to the three different phases of the sample, an example of which is shown in the right hand side of FIG. 3B).

At the same time, radiation source 10 provides radiation beam 12, and the resulting images showing the spatial distribution of the fluorescence are collected by detector element 68a. A typical fluorescence image is shown in the left hand side of FIG. 3B.

The surface profile of the sample $Z_s$ can then be calculated from $$Z_s = \frac{I_{s\,defocused}}{\alpha I_c}$$

where $I_c$ is the conventional reflection image that will be obtained in the absence of a grating, and is given by $$I_c = \frac{1}{3}(I_0 + I_{2\pi/3} + I_{4\pi/3}).$$

The variation in the intensity of the evanescent field, i.e. the radiation used to excite the fluorescence, can be expressed as a function of position along optical axis-Z by $$I(z) = I(0)e^{-4\pi z \lambda^{-1} \sqrt{n_2^2 \sin^2\theta - n_1^2}}$$

where $n_1$ and $n_2$ are the refractive indices of the sample medium 46 and the cover slip 40 respectively, and $\theta$ is the angle between the axis-Z and the incident beam 12 at the cover slip. The modified fluorescence intensity (i.e. the fluorescence intensity that has been adjusted to take into account the incident beam intensity) at each position can then be calculated from $$f = F/I(Z_s)$$

where f is the adjusted fluorescence intensity, and F is the measured fluorescence intensity at each spatial position.

It should be appreciated that the above embodiment is described by way of example only, and that various other implementations will be apparent to the skilled person as falling within the scope of the claims.

For example, whilst FIG. 1 illustrates an apparatus 100 including a TIRF microscope configuration in which fluorescence is measured after travelling back through the optical element in which the excitation beam undergoes total internal reflection, it should be appreciated that the apparatus could be implemented using other TIRF configurations e.g. configurations in which the fluorescence is measured after transmission through the sample.

Further, although in FIG. 2 the beam 12 is illustrated as only undergoing total internal reflection at a single reflection plane of the optical element 40, it should be appreciated that other implementations are possible. For example, the radiation beam could be split into two or more sub-beams, each arranged to undergo total internal reflection from a respective reflection plane. Each reflection plane contains the z-axis. The radiation beam could be split as a function of time e.g. by a Pockel cell, so that the radiation beam alternates between being transmitted along the different paths corresponding to each sub-beam. Each path could impart different characteristics to the radiation beam e.g. one path could correspond to a first polarization state, and a second path to a different polarization state. Alternatively, the radiation beam could be spatially split into two or more sub-beams, so that each sub-beam simultaneously reflects in a respective reflection plane.

Figure 4:
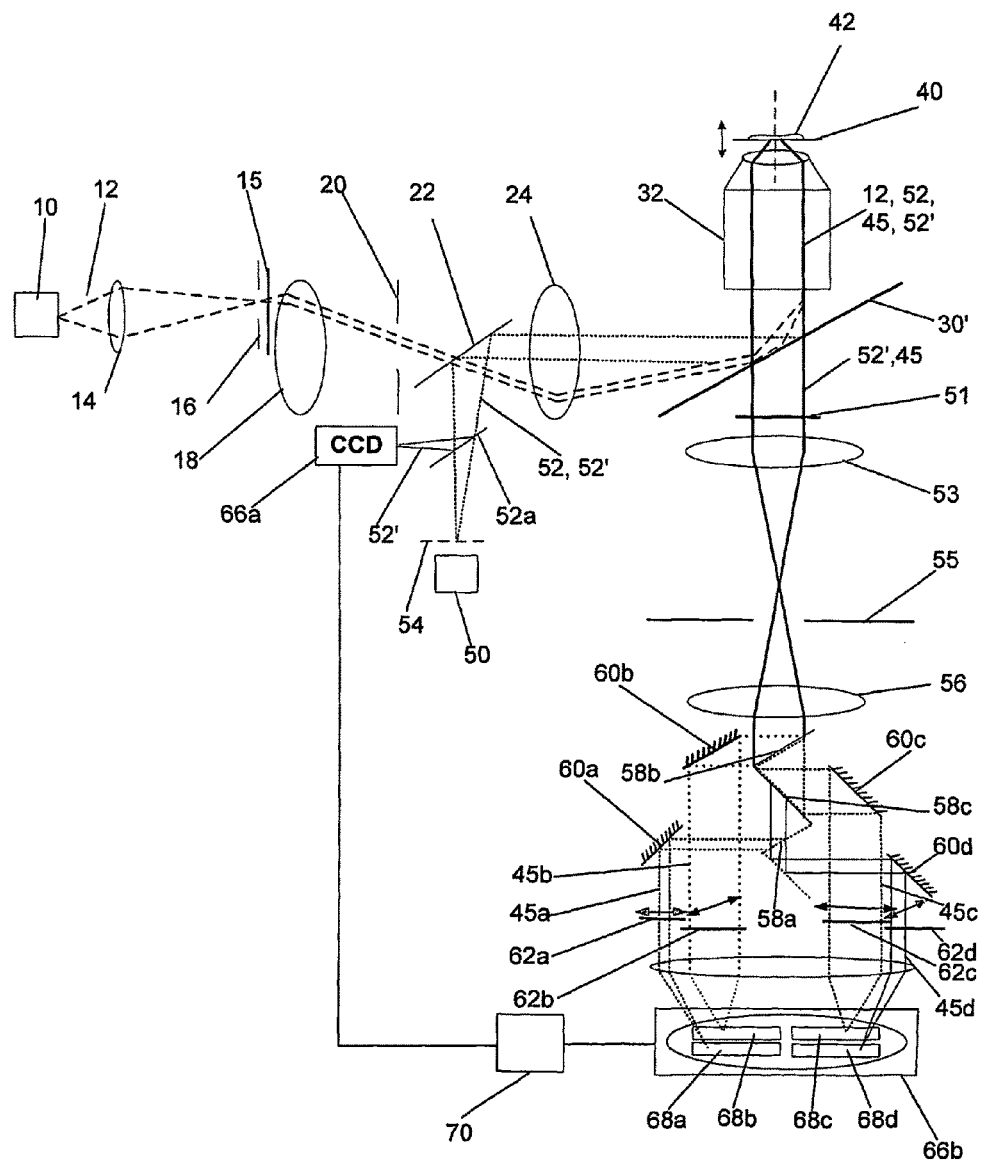
FIG. 4 is a schematic diagram of an apparatus for measuring the fluorescence of a specimen in accordance with a further embodiment of the present invention.

Equally, although in FIG. 1 the reflected beam 52' is shown as being imaged on the same detector 66 as the fluorescence 45, the reflected beam could be imaged on a different detector. FIG. 4 shows such an alternative apparatus configuration 200, in which the reflected beam 52' is imaged on a different detector 66a. In the Figures, identical reference numerals are utilised to represent similar features.

The apparatus 200 achieves this configuration by having dichroic splitter 30' arranged to completely reflect radiation at the wavelength(s) of the beams 52, 52' (rather than act like dichroic splitter 30, which partially reflects and partially transmits such wavelengths). Further the apparatus includes a further beamsplitter 52a located in the optical path of beams 52, 52', such that a portion of the reflected beam 52' is imaged on detector 66a.

In FIG. 1, only a single fluorescence image is captured, by detector element 68a, which would include all relevant fluorescence wavelengths and polarisations. However, the fluorescence 45 can be split by wavelength and/or polarisation. For example, the components of the apparatus 200 used to perform the TIRF measurement could have the configuration described for TIRF measurements in the article by Webb, S. E. D., Needham, S. R., Roberts, S. K. & Martin-Fernandez, M. L. "Multidimensional single-molecule imaging in live cells using total-internal-reflection fluorescence microscopy", Optics Letters 31, 2157-2159 (2006), the contents of which are incorporated herein by reference.

In the implementation shown in FIG. 4, the apparatus 200 is arranged to split the fluorescence 45 by both wavelength (here, into two separate wavelength components) and polarisation (i.e. horizontal and vertical polarisations), but with all components (45a-d) being imaged simultaneously onto respective separate sectors (68a-68d) of a detector 66b. Splitters 58; 58b, 58c act to split the fluorescence 45 into the four components 45a-d, which are each reflected from a respective mirror 60a-d through a respective filter. Respective filters 62a-62d ensure that each sector/element 68a-d of detector 66b only receives one of the wavelength components in one polarisation state.

The apparatus 200 also comprises polarisation element 15 in the optical path of radiation 12. Polarisation element 15 can be implemented as a polarisation plate (arranged to transmit only one polarisation state) and/or a polarization rotator. The polarisation element 15 ensures that the sample is only excited with radiation in a single polarisation state. During operation, whilst the excitation beam 12 is in a first polarised state, a set of images are collected corresponding to the intensities of the different wavelength/polarisation components of the fluorescence. Subsequently, polarisation element 15 is adjusted so as to place the excitation beam 12 in a different polarisation state, and then another set of images are collected corresponding to the intensities of the different wavelength/polarisation components of the fluorescence. For example, this allows measurement of changes in orientation of the dipoles of fluorophores $P_1$, $P_2$.

Various alternatives implementations will be apparent to the skilled person, as falling within the scope of the appended claims.

The invention claimed is:

1. A method of measuring fluorescence from a sample, comprising the steps of:
    measuring at least one profile of at least a portion of a surface of a sample, the surface extending substantially transverse an axis;
    illuminating said portion of the surface of the sample with radiation for stimulating fluorescence, the intensity of the radiation varying with position along the axis; measuring values indicative of the spatial intensity distribution of fluorescence emitted from said portion of the sample surface; and
    modifying the measured values of fluorescence to take account of the spatial variations in intensity of radiation incident upon the surface by utilising said measured profile, wherein said modifying step comprises calculating the spatial variation in intensity of radiation incident on said surface from said measured profile and from information indicative of the variation of the radiation beam intensity with position along the axis.

2. A method as claimed in claim 1, wherein said sample is positioned adjacent an optical element, the illuminating step comprising: providing a radiation beam arranged to undergo total internal reflection within said optical element so as to produce an evanescent field of radiation for exciting fluorophores on the sample surface.

3. A method as claimed in claim 2, wherein said radiation beam is split into two sub-beams, each arranged to undergo total internal reflection in a respective reflection plane.

4. A method as claimed in claim 1, wherein:
    said step of illuminating said portion of the sample surface comprises providing said radiation in a first polarisation state, and
    said step of measuring values comprises measuring values indicative of the spatial intensity distribution of fluorescence emitted in a first polarisation state from said portion of the sample surface, and measuring values indicative of the spatial intensity distribution of fluorescence emitted in a second, different polarisation state from said portion of the sample surface.

5. A method as claimed in claim 4, wherein the step of illuminating said portion of the sample surface further comprises subsequently providing said radiation in a second, different polarisation state for stimulating fluorescence.

6. A method as claimed in claim 1, wherein said step of measuring values comprises:
   measuring values indicative of the spatial intensity distribution of fluorescence emitted in a first wavelength range from said portion of the sample surface, and
   measuring values indicative of the spatial intensity distribution of fluorescence emitted in a second, different wavelength range from said portion of the sample surface.

7. A method as claimed in claim 1, wherein the steps of measuring said profile and measuring said values indicative of the spatial intensity distribution of fluorescence are both repeated over a period of time, for monitoring changes in the conformation of said sample.

8. A method as claimed in claim 1, wherein the steps of measuring said profile and measuring values indicative of the spatial intensity distribution of fluorescence are performed simultaneously.

9. A method as claimed in claim 1, wherein the step of measuring said profile comprises: illuminating said portion of the sample with a radiation beam, and measuring the spatial variation in intensity of the reflected radiation beam.

10. A method as claimed in claim 1, wherein said step of measuring said profile comprises measuring the topography of said at least a portion of the surface of the sample.

11. A method as claimed in claim 10, wherein said topography is measured by non-interferometric widefield optical profilometry.

12. A method as claimed in claim 10, wherein said topography is measured by wide-field optically sectioning microscopy.

13. A method as claimed in claim 1, wherein said sample is a biological cell, the surface of which is defined by a cell membrane.

14. An apparatus for measuring fluorescence from a sample, the apparatus comprising:
   a sample holder for holding a sample such that at least a portion of a surface of the sample extends substantially transverse a predetermined axis;
   a profilometer for measuring at least one profile of said portion of the surface of the sample;
   a radiation source for illuminating said portion of the surface of the sample with radiation for stimulating fluorescence, the intensity of the radiation varying with position along the axis; a detector arranged to measure values indicative of the spatial intensity distribution of fluorescence emitted from said portion of the sample surface; and
   a processor arranged to modify the measured values of fluorescence to take account of the spatial variations in intensity of radiation incident upon the surface by utilising the measured profile, wherein the processor is configured to calculate the spatial variations in intensity of radiation incident on said surface from said measured profile and from information indicative of the variation of the radiation beam intensity with position along the axis.

15. A device for controlling an optical apparatus to carry out a fluorescence measurement, the device comprising:
   a program memory containing processor readable instructions; and
   a processor configured to read and execute instructions stored in said program memory, wherein said processor readable instructions comprise instructions configured to control said apparatus to carry out a method that includes
   measuring at least one profile of at least a portion of a surface of a sample, the surface extending substantially transverse an axis,
   illuminating said portion of the surface of the sample with radiation for stimulating fluorescence, the intensity of the radiation varying with position along the axis; measuring values indicative of the spatial intensity distribution of fluorescence emitted from said portion of the sample surface, and
   modifying the measured values of fluorescence to take account of the spatial variations in intensity of radiation incident upon the surface by utilising said measured profile, wherein said modifying step comprises calculating the spatial variation in intensity of radiation incident on said surface from said measured profile and from information indicative of the variation of the radiation beam intensity with position along the axis.

16. A carrier medium carrying computer readable code configured to cause a computer to carry out a method that includes:
   measuring at least one profile of at least a portion of a surface of a sample, the surface extending substantially transverse an axis;
   illuminating said portion of the surface of the sample with radiation for stimulating fluorescence, the intensity of the radiation varying with position along the axis; measuring values indicative of the spatial intensity distribution of fluorescence emitted from said portion of the sample surface; and
   modifying the measured values of fluorescence to take account of the spatial variations in intensity of radiation incident upon the surface by utilising said measured profile, wherein said modifying step comprises calculating the spatial variation in intensity of radiation incident on said surface from said measured profile and from information indicative of the variation of the radiation beam intensity with position along the axis.

\* \* \* \* \*